United States Patent
Imai

[11] 4,017,150
[45] Apr. 12, 1977

[54] WIDE-ANGLE ILLUMINATING OPTICAL SYSTEM WITH LIGHT GUIDE

[75] Inventor: Toshihiro Imai, Hachiouji, Japan

[73] Assignee: Olympus Optical Co., Ltd., Tokyo, Japan

[22] Filed: Oct. 7, 1975

[21] Appl. No.: 620,503

[30] Foreign Application Priority Data

Oct. 8, 1974 Japan .............................. 49-115872
Nov. 6, 1974 Japan .............................. 49-127833

[52] U.S. Cl. ..................... 350/96 BC; 350/175 SL; 350/231
[51] Int. Cl.² ............................................ G02B 5/16
[58] Field of Search .......... 350/96 BC, 231, 175 SL

[56] References Cited
UNITED STATES PATENTS

| | | | |
|---|---|---|---|
| 2,927,574 | 3/1960 | Scholz | 350/175 SL |
| 2,987,960 | 6/1961 | Sheldon | 350/175 SL |
| 3,132,646 | 5/1964 | Hett | 350/96 BC |
| 3,136,310 | 6/1964 | Meltzer | 350/175 SL |
| 3,145,249 | 8/1964 | Meltzer | 350/175 SL |

*Primary Examiner*—John K. Corbin
*Assistant Examiner*—Stewart Levy
*Attorney, Agent, or Firm*—Cushman, Darby & Cushman

[57] ABSTRACT

A wide-angle illuminating optical system with light guide comprising a positive lens system positioned near the end face of the light guide and arranged to illuminate over a wide observing area by converging the light from the light guide and then diverging said light by means of the positive lens system.

4 Claims, 5 Drawing Figures

WIDE-ANGLE ILLUMINATING OPTICAL SYSTEM WITH LIGHT GUIDE

BACKGROUND OF THE INVENTION 1. a. Field of the Invention

The present invention relates to a wide-angle illuminating optical system with light guide arranged to be capable of illuminating over a wide observing area.

2. b. Description of the Prior Art

In recent years, there is a large tendency for endoscopes to make the observing area large. For this purpose, wide-angle lens systems are developed as optical systems for endoscopes. In known illuminating methods employing a light guide for transmitting the illuminating light such as an optical fiber bundle which have been used for endoscopes, even the theoretical angle covering the illuminating area is 60° and the actual angle covering the effective illuminating area is 50° only. Therefore, even when it is attempted to use an observing objective having a viewing angle exceeding the above-mentioned angle, it is very difficult or impossible to observe the marginal portion of the observing area because such portion is not illuminated satisfactorily or not illuminated at all and, consequently, the wide-angle observing objective cannot display its effect satisfactorily.

To solve the above problem, it is necessary to make the illuminating area of the illuminating light wider so that the above-mentioned wide-angle objective for endoscopes will fully display its effect. For this purpose, it is known to widen the illuminating area by providing a concave lens 2 at the end of the light guide 1 as shown in FIG. 1. This method, however, has the following disadvantages. That is, in endoscopes employing a light guide for illumination, especially in forward-viewing endoscopes of such type, a hood 3 is provided at the distal end of the endoscope in order to prevent the end face of the light guide or front lens surface of the observing objective from closely contacting the surface of the object to be observed. Therefore, in the method illustrated in FIG. 1 in which the field angle of the illuminating optical system is widened by providing a concave lens at the end of the light guide, the illuminating light is partially cut by the hood 3. Moreover, in endoscopes, the end face of the image guide for observation is generally arranged at a position shifted from the position of the end face of the light guide for illumination. Therefore, when the angle covering the illuminating area of the illuminating lens system is about the same as the field angle of the observing lens system, a part of the observing area still becomes dark and, consequently, it is necessary to use an illuminating lens system having a still wider angle.

SUMMARY OF THE INVENTION

It is, therefore, a primary object of the present invention to provide a wide-angle illuminating optical system with light guide comprising a positive lens system positioned near the end of the light guide for transmitting the illuminating light and arranged to illuminate the portion to be observed over a wide area by converging the illuminating light, which is transmitted by the light guide, and then diverging said light by means of said positive lens system.

Another object of the present invention is to provide a wide-angle illuminating optical system with light guide comprising a positive lens system positioned near the end of the light guide and arranged to effectively illuminate the portion to be observed over a wide area by slightly shifting the optical axis of said positive lens system from the center line of the light guide.

BRIEF DESCRITPION OF THE DRAWINGS

DETAILED DESCRIPTION OF THE PREFERRED EMBODIMENTS

Figure 1:
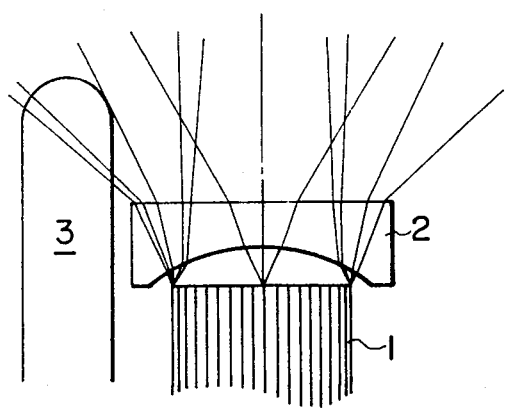
FIG. 1 shows a sectional view of a known wide-angle illuminating optical system with light guide.
Figure 2:
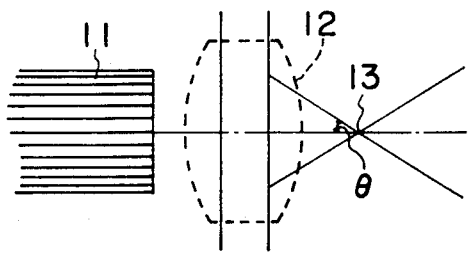
FIG. 2 shows a sectional view for explaining the principle of the present invention.

In the following, concrete content of the present invention is described in detail referring to the accompanying drawings. In FIG. 2, numeral 11 designates a light guide similar to the light guide 1 shown in FIG. 1 and numeral 12 designates a positive lens system. As shown by this figure, the optical system according to the present invention is arranged by providing the positive lens system 12 near the end of the light guide 11 so that the illuminating light from the light guide 11 is once converged at the back focal point 13 of the positive lens system 12 and is then diverged to illuminate the portion to be observed. By the above arrangement, it is possible to make the illuminating field angle wider and also to make the loss of light intensity extremely small.

When reference symbol $f$ represents the focal length of the positive lens system 12, reference symbol $l$ represents the diameter of the light guide 11, reference symbol $\theta$ represents the angle between the optical axis of the optical system and light which comes out from the outermost portion of the light guide in the direction vertical to the end face of the light guide and crosses the optical axis after passing through the optical system, and reference symbol $F_{NO}$ represents the F-number of the optical system, relation of $f$, $l$, $\theta$ and $F_{NO}$ is expressed by the following formulas.

$$F_{NO} = f/l \quad (1)$$

$$\tan \theta = l/2f \quad (2)$$

$$F_{NO} = 1/2 \tan \theta \quad (3)$$

When the fact that each ray itself from the light guide is distributed at an angle nearly 25° is taken into consideration, it is necessary to make the angle $\theta$ 30° or more in order to obtain the illuminating field angle of 70° or more. Therefore, from the formula (3), it becomes $$F_{NO} = 1/2 \tan \theta = 0.866 \quad (4)$$

and, consequently, the F-number becomes as follows.

$$F_{NO} < 0.866 \quad (5)$$

As the positive lens system is to be arranged in a limited space, its outer diameter cannot be made large. If, therefore, the airspace between the end face of the light guide and positive lens system is large, loss of light intensity occurs. Moreover, leakage of light caused after coming out of the light guide and before entering the positive lens system becomes large and, therefore, further loss of light intensity is caused. Therefore, when reference symbol $d$ represents the airspace between the end face of the light guide and positive lens system, it is desirable to select the value of $d$ in the range defined by the following formula.

$$d < \tfrac{1}{2} f$$

Figure 3:
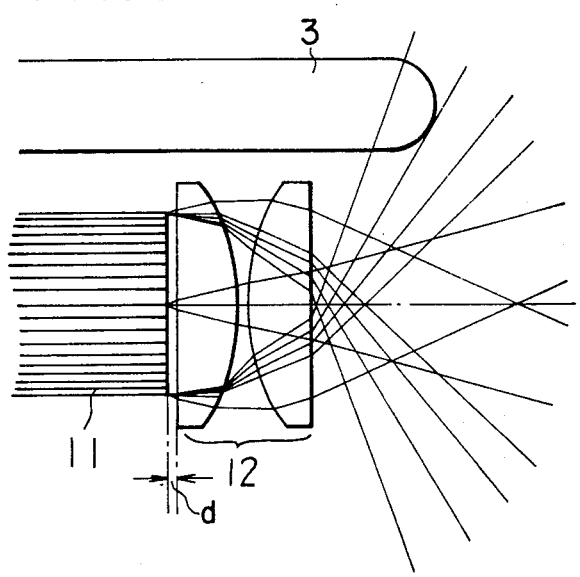
FIG. 3 shows a sectional view illustrating an embodiment of the present invention.

An embodiment of the present invention designed based on the content described in the above has configuration as shown in FIG. 3 and concrete numerical values shown below:

$r_1 = \infty$
$\quad d_1 = 1.1 \qquad n_1 = 1.7859 \qquad \nu_1 = 44.2$
$r_2 = -3.5$
$\quad d_2 = 0.1$
$r_3 = 3.5$
$\quad d_3 = 1.1 \qquad n_2 = 1.7859 \qquad \nu_2 = 44.2$
$r_4 = \infty$ wherein reference symbols $r_1$ through $r_4$ respectively represent radii of curvature of respective lens surfaces of the illuminating lens system 12, reference symbols $d_1$ through $d_3$ respectively represent thicknesses of respective positive lenses and airspace between respective lenses, reference symbols $n_1$ and $n_2$ respectively represent refractive indices of respective lenses, reference symbol $\nu_1$ and $\nu_2$ respectively represent Abbe's numbers of respective lenses.

In this embodiment, it becomes $f = 2.252$, $d = 0.2$ and $l = 3$ and the illuminating field angle is 80° or more. Besides, it is possible to obtain satisfactory illumination in which irregularity is minimized.

Figure 4:
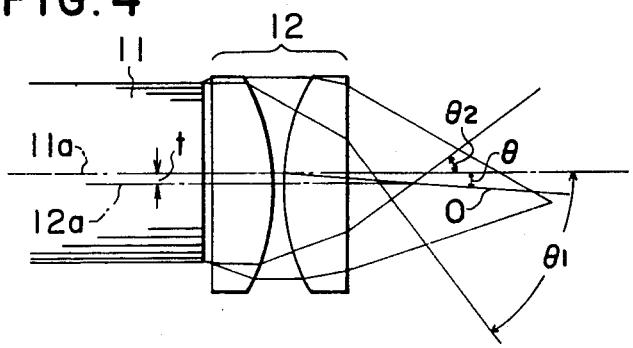
FIG. 4 shows a sectional view illustrating another embodiment of the present invention.

Now, FIG. 4 shows another embodiment of the present invention having configuration different from the embodiment shown in FIG. 3 but comprising the illuminating lens system 12 which is same as the illuminating lens system shown in FIG. 3. In this embodiment, the optical axis 12a of the illuminating lens system 12 is shifted from the center line 11a of the light guide 11 by a small amount $t$ in the direction vertical to the optical axis 12a of the illuminating lens system 12. By the above arrangement, the illuminating area of the light, which is once converged by the lens system 12 and is then diverged, is shifted toward the direction to which the optical axis 12a of the illuminating lens system 12 is shifted. In other words, out of rays diverged as above, the angle $\theta_1$ between the outermost diverging ray on the side to which the illuminating lens system 12 is shifted and the center line 11a of the light guide or the optical axis 12a of the illuminating lens system 12 becomes larger than the angles of rays in the other portion. When, therefore, the optical axis 12a is shifted toward the image guide (toward the observing optical system), it is possible to compensate the difference between the observing area and illuminating area. Consequently, favourable illumination is obtained even for an observing optical system employing a wide-angle lens system and it is possible to favourably observe over a wide area.

In the embodiment shown in FIG. 4, the airspace $d$ between the end face of the light guide 11 and the first lens surface $r_1$ of the illuminating lens system 12 is 0.1, the amount of shifting $t$ between the center line 11a of the light guide and optical axis 12a of the illuminating lens system is 0.2 and, therefore, the angle of deviation $\theta$ of the optical axis 0 of the light passed through the illuminating lens system of the optical system according to the present invention in respect to the center line 11a of the light guide becomes 5° Besides, the angle $\theta_1$ between the center line 11a of the light guide and the outermost ray on the side to which the illuminating lens system is shifted (the lower side in FIG. 4) is 52°9' and the similar angle $\theta_2$ on the opposite side is 35° 57'.

Figure 5:
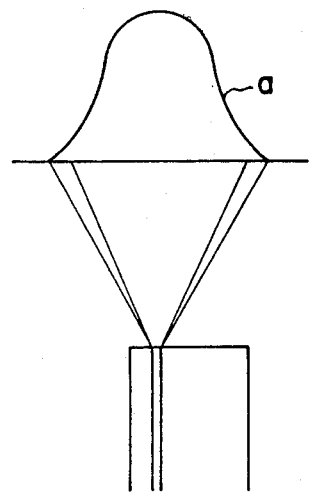
FIG. 5 shows a graph illustrating the distribution of intensity of the illuminating light from an optical fiber.

As explained in the above, according to the present invention, it is possible to illuminate an extremely wide area. Furthermore, for the light coming out of the end face of each optical fiber, the light intensity is distributed as shown by the curva $a$ in FIG. 5, i.e., the light intensity is higher at the center portion and becomes lower toward the marginal portion. Therefore, the rays coming out in the direction vertical to the end face of the optical fiber constitute the most part of the illuminating light. By the lens system according to the present invention, all of these vertical rays are converged at the back focal point of the positive lens system and then diverged in a wide angle. Therefore, it is possible to attain illumination in which irregularity of illumination is minimized.

Besides, when the optical axis of the illuminating lens system is shifted from the center line of the light guide as illustrated by the embodiment shown in FIG. 4, it is possible to favourably illuminate the area to be observed without causing loss of light. Therefore, it is especially effective as it becomes possible to observe extremely favourably over a wide area.

I claim:

1. A wide-angle illuminating optical system with light guide comprising:

a light guide for transmitting the illuminating light and a positive lens system arranged near the end of said light guide, said wide-angle illuminating optical system with light guide being arranged to illuminate a wide area of the portion to be observed by converging the illuminating light from said light guide at the back focal point of said positive lens system and, then, diverging said light, said illuminating optical system satisfying the following conditions:

$$f/l < 0.866 \qquad (1)$$

$$d < \tfrac{1}{2} f \qquad (2)$$

wherein
reference symbol $l$ represents the diameter of said light guide,
reference symbol $d$ represents the airspace between the end face of said light guide and the first lens surface of said positive lens system, and
reference symbol $f$ represents the focal length of said positive lens system.

2. A wide-angle illuminating optical system with light guide according to claim 1, in which said positive lens system consists of two positive lenses and has the following numerical values:

$d = 0.2,\qquad f = 2.252,\qquad l = 3$
$r_1 = \infty$
$\quad d_1 = 1.1 \qquad n_1 = 1.7859 \qquad \nu_1 = 44.2$
$r_2 = -3.5$
$\quad d_2 = 0.1$
$r_3 = 3.5$
$\quad d_3 = 1.1 \qquad n_2 = 1.7859 \qquad \nu_2 = 44.2$ $r_4 = \infty$ wherein reference symbols $r_1$ through $r_4$ respectively represent radii of curvature of respective lens surfaces, reference symbols $d_1$ through $d_3$ respectively represent thicknesses of respective lenses and airspace between respective lenses, reference symbols $n_1$ and $n_2$ respectively represent refractive indices of respective lenses, reference symbols $\nu_1$ and $\nu_2$ respectively represent Abbe's numbers of respective lenses, reference symbol $f$ represents the focal length of the lens system, reference symbol $l$ represents the diameter of the light guide, and reference symbol $d$ represents the airspace between the end face of the light guide and the first lens surface of the lens system.

3. A wide-angle illuminating optical system with light guide according to claim 1, in which said positive lens system is positioned in respect to said light guide so that the optical axis of said positive lens system is shifted from the center line of said light guide.

4. A wide-angle illuminating optical system with light guide according to claim 3, in which said positive lens system consists of two positive lenses and has the following numerical values:

$r_1 = \infty$
$\quad d_1 = 1.1 \qquad n_1 = 1.7859 \qquad \nu_1 = 44.2$
$r_2 = -3.5$
$\quad d_2 = 0.1$
$r_3 = 3.5$
$\quad d_3 = 1.1 \qquad n_2 = 1.7859 \qquad \nu_2 = 44.2$
$r_4 = \infty$
$\quad t = 0.2$ wherein reference symbols $r_1$ through $r_4$ respectively represent radii of curvature of respective lens surfaces, reference symbols $d_1$ through $d_3$ respectively represent thicknesses of respective lenses and airspace between respective lenses, reference symbols $n_1$ and $n_2$ respectively represent refractive indices of respective lenses, reference symbols $\nu_1$ and $\nu_2$ respectively represent Abbe's numbers of respective lenses, reference symbol $t$ represents the amount of shifting between the center line 11a of the light guide and optical axis of the illuminating lens system.

* * * * *